United States Patent [19]

Eisenhuth et al.

[11] Patent Number: 6,159,894
[45] Date of Patent: Dec. 12, 2000

[54] CATALYST FOR DEHYDROGENATION OF AMINO ALCOHOLS TO AMINO CARBOXYLIC ACIDS OR OF ETHYLENE GLYCOL (DERIVATIVES) TO OXYCARBOXYLIC ACIDS, METHOD FOR THEIR PRODUCTION AND THEIR USE

[75] Inventors: Ludwig Eisenhuth, Obernburg; Manfred F. Bergfeld, Erlenbach, both of Germany

[73] Assignee: Akzo Nobel NV, Postbus, Netherlands

[21] Appl. No.: 09/242,560

[22] PCT Filed: Sep. 24, 1997

[86] PCT No.: PCT/EP97/05224

§ 371 Date: Mar. 26, 1999

§ 102(e) Date: Mar. 26, 1999

[87] PCT Pub. No.: WO98/13140

PCT Pub. Date: Apr. 2, 1998

[30] Foreign Application Priority Data

Sep. 26, 1996 [DE] Germany .................... 196 39 474

[51] Int. Cl.⁷ .................... B01J 23/00; C07C 51/16
[52] U.S. Cl. .................... 502/308; 502/227; 502/244; 502/300; 502/305; 502/306; 502/313; 502/314; 562/526; 562/539; 562/553; 562/566; 562/572
[58] Field of Search .................... 502/308, 227, 502/244, 300, 305, 306, 313, 314; 562/526, 539, 553, 572, 566

[56] References Cited

U.S. PATENT DOCUMENTS 5,220,054  6/1993  Urano et al. .
5,292,936  3/1994  Franczyk .
5,367,112  11/1994  Franczyk .
5,739,390  4/1998  Franczyk et al. .

FOREIGN PATENT DOCUMENTS

| 0 506 973 A1 | 10/1992 | European Pat. Off. . |
| 0 513 396 A1 | 11/1992 | European Pat. Off. . |
| 35 05 208 C2 | 3/1986 | Germany . |
| 40 21 230 A1 | 1/1991 | Germany . |
| 61-93146 | 5/1986 | Japan . |
| 2 148 287 | 5/1985 | United Kingdom . |
| 2 164 034 | 3/1986 | United Kingdom . |
| WO 94/24091 | 10/1994 | WIPO . |
| WO 96/01146 | 1/1996 | WIPO . |

*Primary Examiner*—James O. Wilson
*Assistant Examiner*—Robert W. Deemie
*Attorney, Agent, or Firm*—Oliff & Berridge, PLC

[57] ABSTRACT

Catalyst for dehydrogenating amino alcohols to aminocarboxylic acids or ethylene glycol (derivatives) to oxycarboxylic acids, said catalyst containing zirconium, copper and possibly an additional metal, whereby the cited metals are precipitated as hydroxides, washed, dried, calcined, and reduced, preparable in that zirconium hydroxide is precipitated from an aqueous zirconium salt solution using a base until a pH of 4 to 10 is attained, the aqueous solution of a copper salt and possibly of an additional salt is added to the zirconium hydroxide suspension, and by adding further base copper hydroxide and possibly the hydroxide of the metal contained in the additional salt is precipitated until a pH of 8 to 14 is attained, the suspension obtained is filtered, washed, dried, calcined in air at 450 to 600° C. for 2 to 4 hours and finally reduced at 200 to 250° C. in a hydrogen stream for 2 to 4 hours.

22 Claims, No Drawings

CATALYST FOR DEHYDROGENATION OF AMINO ALCOHOLS TO AMINO CARBOXYLIC ACIDS OR OF ETHYLENE GLYCOL (DERIVATIVES) TO OXYCARBOXYLIC ACIDS, METHOD FOR THEIR PRODUCTION AND THEIR USE

DESCRIPTION

The invention relates to a new catalyst suitable for dehydrogenating amino alcohols to aminocarboxylic acids or ethylene glycol (derivatives) to oxycarboxylic acids, said catalyst containing zirconium, copper, and possibly an additional metal, whereby the cited metals are precipitated as hydroxides, washed, dried, calcined, and reduced.

Moreover, the invention relates to a process for preparing a catalyst usable for dehydrogenating amino alcohols to aminocarboxylic acids or ethylene glycol (derivatives) to oxycarboxylic acids, said catalyst containing zirconium, copper and possibly an additional metal, whereby the cited metals are precipitated as hydroxides, washed, dried, calcined, and reduced.

A number of processes have been disclosed for preparing a catalyst for the aforementioned reactions. These processes can be categorized essentially into four groups, which are described in the following.

Anchor catalysts: In WO-A1-96/01146, the preparation of catalysts with anchor metals is described. A noble metal such as gold, platinum, palladium, or ruthenium is bound as a so-called anchor to an alkali-resistant carrier such as zirconium dioxide, titanium dioxide, or carbon. Metals other than noble metals, such as copper, cobalt, nickel, or cadmium, are deposited on the surface of the anchor using a reduction agent such as formaldehyde.

Raney catalysts: In DE-C2-3505208, Raney copper or Raney nickel is used as a catalyst. In EP-A1-0513396, Raney copper is used as a catalyst with specified values for BET area and for nickel content. In EP-A1-0506973, Raney copper is used as a catalyst, whereby aluminum or an aluminum compound is added to the reaction mixture during the catalytic dehydrogenation. In WO-A1-94/24091 and U.S. Pat. No. 5,367,112, Raney copper is used as a catalyst with 10 to 50000 ppm of one of the elements comprising chromium, titanium, niobium, tantalum, zirconium, vanadium, molybdenum, tungsten, cobalt, nickel, bismuth, tin, antimony, lead, germanium, magnesium, and their mixtures.

Impregnated zirconium oxide: In JP-A1-61-93146 and GB-A1-2148287, a catalyst is described whose preparation comprises impregnating zirconium oxide with an aqueous solution of copper nitrate, drying, calcining in air for 6 hours at 500° C., and reducing for 6 hours at 230° C. in a hydrogen stream.

Simultaneous precipitation of zirconium, copper and possibly an additional metal: In JP-A1-61-93146, DE-C2-3505208, EP-A1-0506973, EP-A1-0513396, and GB-A1-2148287, a catalyst is described whose preparation comprises initially preparing an aqueous solution containing zirconium oxychloride and copper nitrate. Aqueous sodium hydroxide is added to this solution, whereby zirconium and copper are simultaneously precipitated as hydroxides. The washed and dried precipitate is calcined in air for 3 hours at 500° C. and reduced for 6 hours at 230° C. in a hydrogen stream. In accordance with WO-A1-94/24091, an aqueous solution is prepared containing zirconium oxychloride octahydrate, copper nitrate trihydrate, and bismuth nitrate pentahydrate or tin nitrate, and the remaining process is as previously described.

The anchor catalysts require expensive noble metals, which constitute 1 to 50 percent by weight of these catalysts. Catalysts made from Raney nickel are pyrogenic and therefore require increased safety expense during handling. The catalysts made from impregnated zirconium oxide and from simultaneously precipitated zirconium and copper require long reaction times for the catalytic dehydrogenation of amino alcohols. For example, in JP-A1-61-93146, a reaction time of 6.5 hours is required for the transformation of tetrahydroxyethylethylenediamine (THEEDA) to the tetrasodium salt of ethylenediamine tetraacetate ($(EDTA)Na_4$) using a catalyst of impregnated zirconium oxide to produce an $(EDTA)Na_4$ yield of 84.5%. Use of the catalyst also described in JP-A1-61-93146 comprising simultaneously precipitated zirconium and copper requires 6 hours to produce $(EDTA)Na_4$ from THEEDA in a yield of 85%.

Therefore, the object of the present invention is to provide a new catalyst for dehydrogenating amino alcohols or ethylene glycol (derivatives) that at least reduces the described disadvantages of the prior art catalysts.

A further object of the present invention is to provide a process for preparing a catalyst for dehydrogenating amino alcohols or ethylene glycol (derivatives) that at least reduces the described disadvantages of the prior art catalyst preparation processes.

The first object is fulfilled by the catalysts of claims 1 to 10.

The further object is fulfilled by a process in which zirconium hydroxide is precipitated from an aqueous zirconium salt solution using a base until a pH of 4 to 10 is attained. The aqueous solution of a copper salt and possibly an additional salt is added to the zirconium hydroxide suspension, and, by adding further base, copper hydroxide and possibly the hydroxide of the metal contained in the additional salt is precipitated until a pH of 8 to 14 is attained. The suspension obtained is filtered, washed, dried, calcined in air at 450 to 600° C. for 2 to 4 hours, and finally reduced at 200 to 250° C. in a hydrogen stream for 2 to 4 hours.

A preferred process approach consists in precipitating zirconium hydroxide by adding base until a pH of 5 to 9 is attained.

A further preferred process approach consists in precipitating copper hydroxide and possibly the hydroxide of the metal contained in the additional salt by adding further base until a pH of 9 to 12 is attained.

In principle, the base used for hydroxide precipitation can be any conventional alkaline or alkaline-earth hydroxide such as sodium hydroxide, potassium hydroxide, magnesium hydroxide, or calcium hydroxide. The use of aqueous sodium hydroxide or calcium hydroxide is preferred. Moreover, the base used for hydroxide precipitation can in principle be any conventional water-soluble amine such as ammonia, methylamine, dimethylamine, or trimethylamine, whereby an aqueous solution of ammonia or trimethylamine is preferred.

In principle, the zirconium salt can be any water-soluble salt of zirconium. Examples are zirconium oxychloride, zirconium sulfate, zirconium oxalate, zirconium nitrate, zirconium acetate, or zirconium perchlorate. The use of zirconium oxychloride, zirconium acetate, or zirconium nitrate as the zirconium salt is preferred.

In principle, the copper salt can be any water-soluble organic or inorganic salt such as copper nitrate, copper chloride, copper sulfate, or copper acetate. The use of copper nitrate, copper chloride, or copper acetate as the copper salt is preferred.

The use of molybdenum pentachloride or the nitrate or chloride of calcium, iron, aluminum, chromium, bismuth, barium, or magnesium as the additional salt is preferred. The salts used in the invention can be anhydrous or contain water of crystallization. Examples of salts with water of crystallization are zirconium oxychloride octahydrate, copper nitrate trihydrate, calcium nitrate tetrahydrate, iron nitrate nonahydrate, bismuth nitrate pentahydrate, and magnesium nitrate hexahydrate.

In general, the weight ratio of zirconium to copper in the salt solutions for preparing the catalyst is 0.5:1 to 10:1. A weight ratio of zirconium to copper of 1:1 to 5:1 is preferred.

The weight ratio of copper to the possibly additional metal contained in the copper salt solution is in general 250:0.1 to 250:10, preferably 250:1 to 250:7.

The catalyst of the invention is used in the form as reduced by hydrogen. That is, the catalyst is used either directly after its preparation or, in the form reduced by hydrogen, stored until use in a hydrogen atmosphere or reduced in a hydrogen stream at 200 to 250° C. for 2 to 4 hours immediately prior to use.

The use of the catalyst of the invention for dehydrogenating amino alcohols to aminocarboxylic acids or ethylene glycol(derivatives) to oxycarboxylic acids can occur as a suspension or an extrudate or be carrier-bound, whereby in principle any alkali-resistant materials are suited as the carrier.

The catalyst of the invention is used for dehydrogenating amino alcohols with 1 to 50 C atoms to aminocarboxylic acids. Examples for the use of the catalyst are the reactions of ethanolamine to glycine, N-methylethanolamine to sarcosine, THEEDA to EDTA, diethanolamine to iminodiacetic acid, N,N-bis(2-hydroxyethyl)isopropylamine to 2-hydroxypropylaminodiacetic acid, or tetrakis (hydroxyethyl)1,2-propylenediamine.

Surprisingly, it has been discovered that using the catalyst of the invention, whose reduction in a hydrogen stream requires only half the time required for the catalyst described in JP-A1-61-93146, the dehydrogenation of amino alcohols to aminocarboxylic acids proceeds significantly faster, the reaction product occurs in higher yield, and there are significantly fewer byproducts than with a catalyst that differs from the catalyst of the invention only in the simultaneous precipitation of zirconium hydroxide and copper hydroxide.

For example, the dehydrogenation of N-methylethanolamine to sarcosine with the catalyst of the invention leads at a threefold higher reaction rate to a 3% higher sarcosine yield and fewer byproducts, for example less than half the quantity of methylamine, than with a catalyst that differs from the catalyst of the invention only in the simultaneous precipitation of zirconium hydroxide and copper hydroxide.

As well in the dehydrogenation of other amino alcohols to aminocarboxylic acids, the catalyst of the invention exhibits similar advantageous properties. For example, the dehydrogenation of THEEDA to the tetrasodium salt of EDTA ((EDTA)Na$_4$) using the catalyst of the invention, containing zirconium, copper, and calcium, leads to a 1.5% higher (EDTA)Na$_4$ yield at 1.33 times the reaction rate and to significantly lower byproduct generation than with a catalyst that differs from the catalyst of the invention only in the simultaneous precipitation of zirconium hydroxide, copper hydroxide, and calcium hydroxide.

It has also been observed that in the dehydrogenation of amino alcohols containing primary and secondary hydroxyl groups, the catalyst of the invention leads to dehydrogenation only on the primary hydroxyl group. For example, in the dehydrogenation of 2-hydroxypropanoldiethanolamine, only the hydroxyl groups bound to the ethanol residues are oxidized to carboxylic acids, while the hydroxyl group on the propanol residue remains unchanged.

The catalyst of the invention is also used for dehydrogenation of ethylene glycol (derivatives). This includes oligo or polymer ethylene glycols such as triethylene glycol, which is converted to the disodium salt of 3.5.dioxahexanedicarboxylic acid.

Moreover, it includes ethylene glycol derivatives, such as 2-methoxyethanol, which is dehydrogenated to the Na salt of methoxyacetic acid.

Preparation of the catalyst of the invention and its application in dehydrogenation reactions will be described in more detail with reference to the following examples and comparative examples.

EXAMPLE 1

Catalyst preparation: Zirconium hydroxide is precipitated from a solution of 116.65 g zirconium oxychloride octahydrate (362 mmol) in 1.8 liters water by adding 25% aqueous caustic soda solution until a pH of 7 is attained. A solution of 18.84 g copper nitrate trihydrate (78 mmol) in 400 ml water is added to the zirconium hydroxide suspension and copper hydroxide is subsequently precipitated by adding further 25% aqueous caustic soda until a pH of 10.5 is attained. The suspension is filtered, washed chloride-free with water, and dried. The solid is calcined for 3 hours at 490° C., reduced in a hydrogen stream for 3 hours at 230° C., and stored in a hydrogen atmosphere.

Catalyst application: In an autoclave containing a hydrogen atmosphere, 32 g of the catalyst prepared as described in Example 1 is placed with a solution of 90 g methylethanolamine (1.2 mol) and 56 g sodium hydroxide in 135 g water. The autoclave is sealed, filled with hydrogen to a pressure of 5 bar, and subsequently brought to the reaction temperature of 170° C. The reaction is conducted while stirring. As much of the hydrogen formed during the reaction is continuously released from the autoclave as is necessary to maintain the pressure in the autoclave at 12 bar. The hydrogen released from the reactor during the reaction contains the byproduct methylamine, which is determined by titration with hydrochloric acid in a washer. The end of the hydrogen formation indicates the end of the reaction. When the reaction ceases, the reaction solution is removed from the reaction via a filter cartridge and analyzed chromatographically (HPLC). After 2 hours reaction time, sarcosine is produced with a yield of 97%, whereby 24 mmol methylamine is generated.

COMPARATIVE EXAMPLE 1

Catalyst preparation: 274.2 g zirconium oxychloride octahydrate (851 mmol) and 44.2 g copper nitrate trihydrate are dissolved in 2.5 liters water. From this solution, the hydroxides of zirconium and copper are simultaneously precipitated by adding 25% caustic soda solution until a pH of 10.5 is attained. Subsequently as in Example 1 the product is filtered, washed dried, calcined, and reduced.

Catalyst application: The catalyst prepared in Comparative example 1 is employed under the conditions of Example 1 for dehydrogenating N-methylethanolamine to sarcosine. After 6 hours reaction time, sarcosine is produced with a yield of 94%, whereby 54 mmol methylamine is generated.

EXAMPLE 2

Catalyst preparation: Zirconium hydroxide is precipitated from a solution of 116.65 g zirconium oxychloride octahydrate (362 mmol) in 1.8 liters water by adding 25% aqueous caustic soda solution until a pH of 7 is attained. A solution of 29.47 g copper nitrate trihydrate (122 mmol) and 1.16 g calcium nitrate tetrahydrate (4.9 mmol) in 400 ml water is added to the zirconium hydroxide suspension and copper hydroxide and calcium hydroxide are subsequently precipitated by adding further 25% aqueous caustic soda until a pH of 10.5 is attained. The suspension is filtered, washed chloride-free with water, and dried. The solid is calcined for 3 hours at 490° C., reduced in a hydrogen stream for 3 hours at 230° C., and stored in a hydrogen atmosphere.

Catalyst application: 32 g of the catalyst prepared as described in Example 2 is placed with a solution of 71 g tetrahydroxyethyl-ethylenediamine (THEEDA) of 95.5% purity (287 mmol pure THEEDA), 50.8 g sodium hydroxide (1.27 mmol) and 135 g water in an autoclave containing a hydrogen atmosphere. The autoclave is sealed, filled with hydrogen to a pressure of 1 bar and subsequently brought to the reaction temperature of 195 to 200° C. The reaction is conducted while stirring. As much of the hydrogen formed during the reaction is continuously released from the autoclave as is necessary to maintain the pressure in the autoclave at 15 bar. The end of the hydrogen formation indicates the end of the reaction. When the reaction ceases, the reaction solution is removed from the reactor via a filter cartridge and analyzed chromatographically (HPLC). After 2.25 hours reaction time, the tetrasodium salt of ethylenediaminetetraacetic acid ((EDTA)Na$_4$) is formed with a yield of 94.5%, with respect to the initial quantity of THEEDA.

COMPARATIVE EXAMPLE 2

Catalyst preparation: 116.65 g zirconium oxychloride octahydrate (362 mmol), 29.47 g copper nitrate trihydrate (122 mmol), and 1.16 g calcium nitrate tetrahydrate (4.9 mmol) are dissolved in 2.2 liters water. From this solution, the hydroxides of zirconium, copper, and calcium are simultaneously precipitated by adding 25% caustic soda solution until a pH of 10.5 is attained. Subsequently, the result is filtered as in Example 2, washed, dried, calcined, and reduced.

Catalyst application: The catalyst prepared in Comparative example 2 is employed under the conditions of Example 2 for dehydrogenating EDTA to (EDTA)Na$_4$. After 3 hours reaction time, (EDTA)Na$_4$ is produced with a yield of 93%.

EXAMPLE 3

Zirconium hydroxide is precipitated from a solution of 116.65 g ZrOCl$_2$.8H$_2$O (362 mmol) in 1.8 liters water by adding 25% aqueous NaOH until a pH of 7 is attained. A solution of 62.75 g Cu(NO$_3$)$_2$.3H$_2$O (260 mmol) and 0.39 g Ca(NO$_3$)$_2$.4H$_2$O (1.7 mmol) in 400 ml water is added to the zirconium hydroxide suspension, and copper hydroxide and calcium hydroxide are subsequently precipitated by adding further 25% NaOH until a pH of 10.5 is attained. The suspension is filtered, washed chloride-free with water, and dried. The solid is calcined for 3 hours at 490° C. Immediately before the catalyst applications described in the subsequent examples, the solid is reduced in a hydrogen stream for 3 hours at 230° C.

EXAMPLE 4

32 g of the catalyst prepared as described in Example 3 is placed with 71 g THEEDA of 95.5% purity (287 mmol pure THEEDA), 122 9 water, and 50.8 g NaOH (1.27 mmol) in an autoclave containing a hydrogen atmosphere. The autoclave is sealed, brought to a pressure of 5 bar and subsequently to the reaction temperature of 195 to 200° C. The reaction is conducted while stirring. As much of the hydrogen formed during the reaction is continuously released from the autoclave as is necessary to maintain the pressure in the autoclave at 15 bar. After 30 minutes, only slight hydrogen formation is observable. After 2 hours, hydrogen formation has practically ceased, which indicates the end of the reaction. The solid catalyst is filtered off in a hydrogen atmosphere. Concentrated hydrochloric acid is added to the solution at 75° C. until a pH of 1 is attained, whereby 81 g EDTA is obtained, representing a yield of 96.9% with respect to the initial THEEDA quantity. The EDTA purity determined by titration with ZnCl$_2$ is 99%.

EXAMPLE 5

Under the conditions of Example 4, except that the NaOH quantity is increased to 55.6 g (1.39 mmol), EDTA in a yield of 97.5% and a purity of 99% is produced after a reaction time of 2 hours.

EXAMPLE 6

Example 6 was performed under the conditions of Example 4, except that the THEEDA is not part of the initial preparation but rather added over 15 minutes at 190° C. After a reaction time of 2 hours, (EDTA)Na$_4$ is obtained in a yield of 97.6% with respect to the THEEDA added, as determined by HPLC.

EXAMPLE 7

100 g diethanolamine (0.95 mol), 89.6 g NaOH (2.24 mol) in 184 g water, and 32 g of the catalyst prepared as in Example 3, but reduced in the hydrogen stream for only 2 hours at 230° C., are placed in an autoclave. The autoclave is sealed, brought to a pressure of 1 bar and subsequently to the reaction temperature of 160° C. The reaction is conducted while stirring. As much of the hydrogen formed during the reaction is continuously released from the autoclave as is necessary to maintain the pressure in the autoclave at 10 bar. When the reaction has terminated, the reaction solution is removed from the reactor in a hydrogen atmosphere by decanting and filtration. To the solid catalyst remaining in the reactor, 100 g diethanolamine, 89.6 g NaOH, and 184 g water are again added, and the reaction is initiated as just described. In this manner, 10 reaction cycles are conducted, whereby the individual cycles require the following reaction times listed in Table 1:

TABLE 1

Reaction time as a function of cycle number

| Cycle | | | | |
|---|---|---|---|---|
| 1 | 2 | 3 | 4, 5, 6, 7, 8 | 9, 10 |
| t(min) 75 | 80 | 90 | each 115 | each 120 |

After each cycle, the disodium salt of iminodiacetic acid is produced in a yield of >98% and a purity of >98% (analysis with $^{13}$C-NMR and HPLC).

EXAMPLE 8

90 g N-methylethanolamine (1.2 mol), 56 g NaOH (1.4 mol), 135 g water, and 32 g of the catalyst prepared in Example 7 are placed in an autoclave. The autoclave is sealed, brought to a pressure of 5 bar, and then to the reaction temperature of 170° C. The reaction is conducted while stirring. As much of the hydrogen formed during the reaction is continuously released from the autoclave as is necessary to maintain the pressure in the autoclave at 10 bar. The hydrogen released from the reactor during the reaction contains the byproduct methylamine, which is determined as in Example 1. When the reaction ceases, the reaction solution is removed from the reactor in a hydrogen atmosphere by decanting and filtration. 90 g N-methylethanolamine, 56 g NaOH and 135 g water are again added to the solid catalyst remaining in the reactor, and the reaction is initiated as just described. In this manner, 10 reaction cycles are conducted, whereby the individual cycles require the following reaction times listed in Table 2:

TABLE 2

Reaction time as a function of cycle number

| | Cycle | | |
|---|---|---|---|
| | 1 | 2, 3, 4, 5, 6, 7, 8 | 9, 10 |
| t(min) | 125 | each 105 | each 110 |

After each cycle, the sodium salt of sarcosine is produced in a yield of >98% (analysis by HPLC). Per cycle, 12 mmol of methylamine was identified in the exhaust vapor.

EXAMPLE 9

49 9 N,N-bis(2-hydroxyethyl)isopropylamine (0.3 mol), 25.2 g NaOH (0.6 mol), 135 g water, and 32 g of the catalyst prepared in Example 7 are placed in an autoclave. The autoclave is sealed, brought to a pressure of 5 bar, and then to the reaction temperature of 175° C. The reaction is conducted while stirring. As much of the hydrogen formed during the reaction is continuously released from the autoclave as is necessary to maintain the pressure in the autoclave at 12 bar. After 90 minutes, hydrogen is no longer produced. After filtration and freeze drying, 2-hydroxypropylaminodiacetic acid is produced in a yield of 99% and a purity of >99%, as analyzed by $^{13}$C-NMR.

EXAMPLE 10

116.9 g N-phenylethanolamine (0.95 mol), 41.7 g NaOH (1.04 mol) in 270 g water, and 32 g of the catalyst prepared in Example 3, but reduced in a hydrogen stream for only 2 hours at 230° C., are placed in an autoclave. The autoclave is sealed, brought to a pressure of 5 bar, and then to the reaction temperature of 195° C. The reaction is conducted while stirring. As much of the hydrogen formed during the reaction is continuously released from the autoclave as is necessary to maintain the pressure in the autoclave at 14 bar. After 135 minutes, the theoretical quantity of hydrogen has been formed, and the reaction ceases. After freeze and spray drying, the Na salt of phenylglycine is obtained as a white powder in a yield of >97% and a purity of >96%, as analyzed by $^{13}$C-NMR.

EXAMPLE 11

37.5 g tetrakis(hydroxyethyl)1,2-propylenediamine (0.15 mol), 25.6 g NaOH (0.64 mol), 122 g water, and 32 g of the catalyst prepared in Example 7 are placed in an autoclave. The autoclave is sealed, brought to a pressure of 5 bar, and then to the reaction temperature of 199° C. The reaction is conducted while stirring. As much of the hydrogen formed during the reaction is continuously released from the auto-clave as is necessary to maintain the pressure in the autoclave at 15 bar. After a reactions time of 1.5 hours and freeze drying, the Na salt of the 1,2-propylenediaminetetraacetic acid is obtained as a white powder in a yield of >96% and a purity of >95%, as analyzed by $^{13}$C-NMR. By acidification with concentrated hydrochloric acid, 1,2-propylenediaminetetraacetic acid is obtained as a white powder in a yield of 91%.

EXAMPLE 12

91.3 g 2-methoxyethanol (1.2 mol), 56 g NaOH (1.4 mol) in 135 g water, and 32 9 of the catalyst prepared as in Example 3, but reduced for only 2 hours at 230° C. in a hydrogen stream, are placed in an autoclave. The autoclave is sealed, brought to a pressure of 5 bar, and then to the reaction temperature of 188° C. The reaction is conducted while stirring. As much of the hydrogen formed during the reaction is continuously released from the autoclave as is necessary to maintain the pressure in the autoclave at 11 bar. Release of hydrogen is performed via a condenser, whose cooling capacity is such that there is no appreciable loss of the alcohol in connection with the release of hydrogen. After a reaction time of 130 minutes and freeze drying, the Na salt of the methoxyacetic acid is obtained as a white solid in a yield of >99% and a purity of >98%, as analyzed by $^{13}$C-NMR.

EXAMPLE 13

90.1 g triethylene glycol (0.6 mol), 46 g NaOH (1.2 mol) in 184 g water, and 32 g of the catalyst prepared as in Example 3, but reduced for only 2 hours at 230° C. in a hydrogen stream, are placed in an autoclave. The autoclave is sealed, brought to a pressure of 5 bar and then to the reaction temperature of 180° C. The reaction is conducted while stirring. As much of the hydrogen formed during the reaction is continuously released from the autoclave as is necessary to maintain the pressure in the autoclave at 10 bar. After a reaction time of 210 minutes and freeze drying, the Na salt of the 3.5.dioxahexanedicarboxylic acid is produced as a white solid in a yield of >99% and a purity of >98%, as analyzed by $^{13}$C-NMR.

EXAMPLE 14

Catalyst preparation: The catalyst was prepared as in Example 3, except that in the precipitation of zirconium hydroxide by addition of NaOH a pH of 5 rather than 7 was established.

Catalyst application: The catalyst was used as in Example 4, except that the amount of water used was increased to 183 g. After a reaction time of 120 minutes, the tetrasodium salt of EDTA was produced in a yield of 93.4%, as determined by HPLC.

EXAMPLE 15

Preparation and application of the catalyst were as in Example 14, except that in the precipitation of zirconium hydroxide a pH of 9 rather than 5 was established. After a reaction time of 120 minutes, the tetrasodium salt of EDTA was produced in a yield of 93.8%, as determined by HPLC.

What is claimed is:

1. Catalyst for dehydrogenating amino alcohols to aminocarboxylic acids or ethylene glycol (derivatives) to oxycarboxylic acids, said catalyst containing zirconium, copper and possibly an additional metal, whereby the cited metals are precipitated as hydroxides, washed, dried, calcined, and reduced, preparable in that zirconium hydroxide is precipitated from an aqueous zirconium salt solution using a base until a pH of 4 to 10 is attained, the aqueous solution of a copper salt and possibly of an additional salt is added to the zirconium hydroxide suspension, and, by adding further base, copper hydroxide and possibly the hydroxide of the metal contained in the additional salt is precipitated until a pH of 8 to 14 is attained, the suspension obtained is filtered, washed, dried, calcined in air at 450 to 600° C. for 2 to 4 hours and finally reduced at 200 to 250° C. in a hydrogen stream for 2 to 4 hours.

2. Catalyst in accordance with claim 1, characterized in that zirconium hydroxide is precipitated from an aqueous zirconium salt solution using a base until a pH of 5 to 9 is attained.

3. Catalyst in accordance with claim 1, preparable in that by adding further base copper hydroxide and possibly the hydroxide of the metal contained in the additional salt is precipitated until a pH of 9 to 12 is attained.

4. Catalyst in accordance with claim 1, preparable in that the base is an aqueous solution of an alkaline or alkaline-earth hydroxide or of an amine.

5. Catalyst in accordance with claim 4, preparable in that the alkaline hydroxide is sodium hydroxide, the alkaline-earth hydroxide is calcium hydroxide, and the amine is ammonia or trimethylamine.

6. Catalyst in accordance with claim 1, preparable in that the zirconium salt is zirconium oxychloride, zirconium sulfate, zirconium oxalate, zirconium nitrate, zirconium acetate, or zirconium perchlorate, the copper salt is copper nitrate, copper chloride, copper sulfate, or copper acetate, and the additional salt is molybdenum pentachloride or the nitrate or chloride of calcium, iron, aluminum, chromium, bismuth, barium, or magnesium, whereby the salts contain water of crystallization or are anhydrous.

7. Catalyst in accordance with claim 1, preparable in that the weight ratio of zirconium to copper is 0.5:1 to 10:1.

8. Catalyst in accordance with claim 7, preparable in that the weight ratio of zirconium to copper is 1:1 to 5:1.

9. Catalyst in accordance with claim 1, preparable in that the weight ratio of copper to the additional metal is 250:0.1 to 250:10.

10. Catalyst in accordance with claim 9, preparable in that the weight ratio of copper to the additional metal is 250:1 to 250:7.

11. Process for preparing a catalyst for dehydrogenating amino alcohols to aminocarboxylic acids or ethylene glycol (derivatives) to oxycarboxylic acids, said catalyst containing zirconium, copper and possibly an additional metal, whereby the cited metals are precipitated as hydroxides, washed, dried, calcined, and reduced, characterized in that zirconium hydroxide is precipitated from an aqueous zirconium salt solution using a base until a pH of 4 to 10 is attained, the aqueous solution of a copper salt and possibly of an additional salt is added to the zirconium hydroxide suspension, and, by adding further base, copper hydroxide and possibly the hydroxide of the metal contained in the additional salt is precipitated until a pH of 8 to 14 is attained, the suspension obtained is filtered, washed, dried, calcined in air at 450 to 600° C. for 2 to 4 hours and finally reduced at 200 to 250° C. in a hydrogen stream for 2 to 4 hours.

12. Process in accordance with claim 11, characterized in that zirconium hydroxide is precipitated from an aqueous zirconium salt solution using a base until a pH of 5 to 9 is attained.

13. Process in accordance with claim 11, characterized in that by adding further base copper hydroxide and possibly the hydroxide of the metal contained in the additional salt is precipitated until a pH of 9 to 12 is attained.

14. Process in accordance with claim 11, characterized in that the base is an aqueous solution of an alkaline or alkaline-earth hydroxide or of an amine.

15. Process in accordance with claim 14, characterized in that the alkaline hydroxide is sodium hydroxide, the alkaline-earth hydroxide is calcium hydroxide, and the amine is ammonia or trimethylamine.

16. Process in accordance with claim 11, characterized in that the zirconium salt is zirconium oxychloride, zirconium sulfate, zirconium oxalate, zirconium nitrate, zirconium acetate, or zirconium perchlorate, the copper salt is copper nitrate, copper chloride, copper sulfate, or copper acetate, and the additional salt is molybdenum pentachloride or the nitrate or chloride of calcium, iron, aluminum, chromium, bismuth, barium, or magnesium, whereby the salts either contain water of crystallization or do not contain water of crystallization.

17. Process in accordance with claim 11, characterized in that the weight ratio of zirconium to copper is 0.5:1 to 10:1.

18. Process in accordance with claim 17, characterized in that the weight ratio-of zirconium to copper is 1:1 to 5:1.

19. Process in accordance with claim 11, characterized in that the weight ratio of copper to the additional metal is 250:0.1 to 250:10.

20. Process in accordance with claim 19, characterized in that the weight ratio of copper to the additional metal is 250:1 to 250:7.

21. A process for dehydrogenating amino alcohols to aminocarboxylic acids using a catalyst from claim 1.

22. A process for dehydrogenating ethylene glycol derivatives to oxycarboxylic acids using a catalyst from claim 11.

* * * * *

UNITED STATES PATENT AND TRADEMARK OFFICE
CERTIFICATE OF CORRECTION

PATENT NO. : 6,159,894
DATED : December 12, 2000
INVENTOR(S) : Ludwig Eisenhuth and Manfred F. Bergfeld It is certified that error appears in the above-identified patent and that said Letters Patent is hereby corrected as shown below:

Title page,
Item [54], change "CATALYST FOR DEHYDROGENATION OF AMINO ALCOHOLS TO AMINO CARBOXYLIC ACIDS OR OF ETHYLENE GLYCOL (DERIVATIVES) TO OXYCARBOXYLIC ACIDS, METHOD FOR THEIR PRODUCTION AND THEIR USE" to -- CATALYST FOR DEHYDROGENATING AMINO ALCOHOLS TO AMINOCARBOXYLIC ACIDS OR ETHYLENE GLYCOL (DERIVATIVES) TO OXYCARBOXYLIC ACIDS, PROCESS FOR ITS PREPARATION AND APPLICATION THEREOF --;
Item [73], change "POSTBUS" to -- ARNHEM --.

Column 1,
Lines 1-6, change "CATALYST FOR DEHYDROGENATION OF AMINO ALCOHOLS TO AMINO CARBOXYLIC ACIDS OR OF ETHYLENE GLYCOL (DERIVATIVES) TO OXYCARBOXYLIC ACIDS, METHOD FOR THEIR PRODUCTION AND THEIR USE" to -- CATALYST FOR DEHYDROGENATING AMINO ALCOHOLS TO AMINOCARBOXYLIC ACIDS OR ETHYLENE GLYCOL (DERIVATIVES) TO OXYCARBOXYLIC ACIDS, PROCESS FOR ITS PREPARATION AND APPLICATION THEREOF --.

Column 5,
Line 49, change "$ZrOCl_2.8H_2O$" to -- $ZrOCl_2 \cdot 8H_2O$ --;
Line 51, change "$Cu(NO_3)_2.3H_2O$" to -- $Cu(NO_3)_2 \cdot 3H_2O$ --;
Line 52, change "$Ca(NO_3)_2.4H_2O$" to -- $Ca(NO_3)_2 \cdot 4H_2O$ --;
Line 65, change "122 9" to -- 122 g --.

UNITED STATES PATENT AND TRADEMARK OFFICE
CERTIFICATE OF CORRECTION

PATENT NO. : 6,159,894
DATED : December 12, 2000
INVENTOR(S) : Ludwig Eisenhuth and Manfred F. Bergfeld It is certified that error appears in the above-identified patent and that said Letters Patent is hereby corrected as shown below:

Column 7,
Line 30, change "49 9" to -- 49 g --.

Column 8,
Line 13, change "32 9" to -- 32 g --.

Column 10,
Line 39, change "ratio-of" to -- ratio of --.

Signed and Sealed this

Twenty-fifth Day of September, 2001

Attest:

NICHOLAS P. GODICI
Attesting Officer    Acting Director of the United States Patent and Trademark Office